United States Patent [19]

Zaiger

[11] Plant 4,519

[45] Apr. 8, 1980

[54] CHERRY TREE

[76] Inventor: Chris F. Zaiger, 537 Rosemore Ave., Modesto, Calif. 95351

[21] Appl. No.: 775

[22] Filed: Dec. 19, 1978

[51] Int. Cl.[2] ..... A01H 5/03
[52] U.S. Cl. ..... Plt./37
[58] Field of Search ..... Plt./37

*Primary Examiner*—Robert E. Bagwill
*Assistant Examiner*—James R. Feyrer

[57] ABSTRACT

An new and distinct variety of self fertile cherry tree which is of small size, (approximately $\frac{1}{3}$ to $\frac{1}{2}$), semi-spreading in growth; the tree being a regular and productive bearer of large, firm, red fruit of good eating and shipping quality.

1 Drawing Figure

ORIGIN OF THE VARIETY

The present variety of cherry tree was originated by me in my experimental orchard located at Modesto, Calif. as a seedling of a cross between Garden Bing (U.S. Plant Pat. No. 3,810) and a seedling which originated from an open pollenated seed of Stella Cherry. The seedlings were kept under careful and continuing observation and one seedling recognized for its distinct and desirable characteristics described above was selected for reproduction and ultimate introduction into the commercial trade.

ASEXUAL REPRODUCTION OF THE VARIETY

The present variety of cherry tree was propagated by me by budding at my experimental orchard located at Modesto, Calif. and such reproductions run true to form with the original cherry tree.

SUMMARY OF THE VARIETY

The present variety of self fertile cherry tree is a regular and productive bearer of large, firm, red fruit of good eating and shipping quality; the tree is further characterized by being semi-dwarf, reaching 12–15 feet in eight years, medium dense and semi-spreading in growth habit.

BRIEF DESCRIPTION OF THE DRAWING

The drawing is an illustration by photographic reproduction in color showing typical specimens of the foliage, with leaves showing the upper and lower surfaces, and with clusters of fruit showing the fruit shape and surface color and a portion of branch showing the close leaf nodes and fruit spurs. The photographs were taken shortly after picking and the color is as nearly true as reasonably possible in a color representation of this type.

DESCRIPTION OF THE VARIETY

The following is a botanical description of this new and distinct variety of cherry tree and its fruit, with color definitions (except those in common terms) referenced to Reinhold color Atlas, by A. Korneruf and J. H. Wanscher as based upon observations of specimens grown at Modesto, Calif.

Tree:
- *Size.*—Small, semi-dwarf. Approximately $\frac{1}{3}$ to $\frac{1}{2}$ normal size.

- *Vigor.*—Semi-vigorous.
- *Growth.*—Semi-spreading.
- *Density.*—Medium dense.
- *Productivity.*—Productive.
- *Bearer.*—Regular.

Trunk:
- *Size.*—Medium stocky.
- *Texture.*—Medium.

Branches:
- *Size.*—Medium stocky.
- *Color.*—Brown to reddish brown.
- *Lenticels.*—Medium to large size. Medium number.

Leaves:
- *Size.*—Medium. Average length — $5\frac{3}{4}''$. Average width — $2\frac{1}{8}''$.
- *Form.*—Ovate.
- *Thickness.*—Medium.
- *Margin.*—Serrate.
- *Petiole.*—Average length — $1\frac{1}{2}''$. Average thickness — 5/64".
- *Glands.*—Average number 2. Primarily on petiole. Reniform.
- *Color.*—Upper side — dark green (27-F-8 to 28-F-7). Under side — grayish green (28-D-5 to 28-D-7).

Flowers buds:
- *Size.*—Large.
- *Length.*—Medium.
- *Form.*—Plump.

Flowers:
- *Blooming period.*—Date of first bloom: Mar. 19, 1978. Date of full bloom: Mar. 24, 1978.
- *Color.*—White.

Fruit:
- *Maturity when described.*—Eating ripe June 12, 1978.
- *Size.*—Uniform — Large. Average diameter axially $1\frac{1}{4}''$. Average transversely in suture plane — $1\frac{1}{8}''$.
- *Form.*—Uniform — Globose to slightly oblate.
- *Suture.*—Shallow — apex to stem end. Smooth — slightly darker red in color.
- *Cavity.*—Circular. Depth — $\frac{1}{8}''$. Width — $\frac{1}{4}''$.
- *Base.*—Rounded to nearly flat.
- *Apex.*—Rounded to slightly depressed.

Skin:
- *Thickness.*—Medium.
- *Texture.*—Medium.
- *Down.*—Wanting.

*Color.*—Red — (10-B-8 to 11-C-8).

Flesh:

*Texture.*—Firm, crisp — meaty.

*Ripens.*—Relatively even.

*Flavor.*—Sub-acid.

*Eating quality.*—Good.

*Color of flesh.*—Pink.

Stone:

*Type.*—Semi-freestone. Adheres to flesh slightly along ventral edge.

*Size.*—Average length — 7/16". Average breadth — $\frac{3}{8}$". Average thickness — $\frac{1}{4}$".

*Form.*—Oblong.

*Tendency to split.*—None.

*Color.*—Light tan.

Stem of fruit:

*Size.*—Average length — $1\frac{3}{8}$". Average thickness — 3/32".

Use: Local and long distance markets. Dessert.

Keeping quality: Excellent.

Shipping: Excellent.

The tree and its fruit herein described as grown near Modesto, Calif., may vary in slight detail due to soil conditions, climate and cultural practices under which the variety may be grown.

I claim:

1. A new and distinct variety of cherry tree as described and illustrated, characterized particularly by being semi-dwarf in size, reaching 12–15 feet in 8 years, semi-spreading in growth, self fertile and a regular and productive bearer of large, firm fruit of good eating quality.

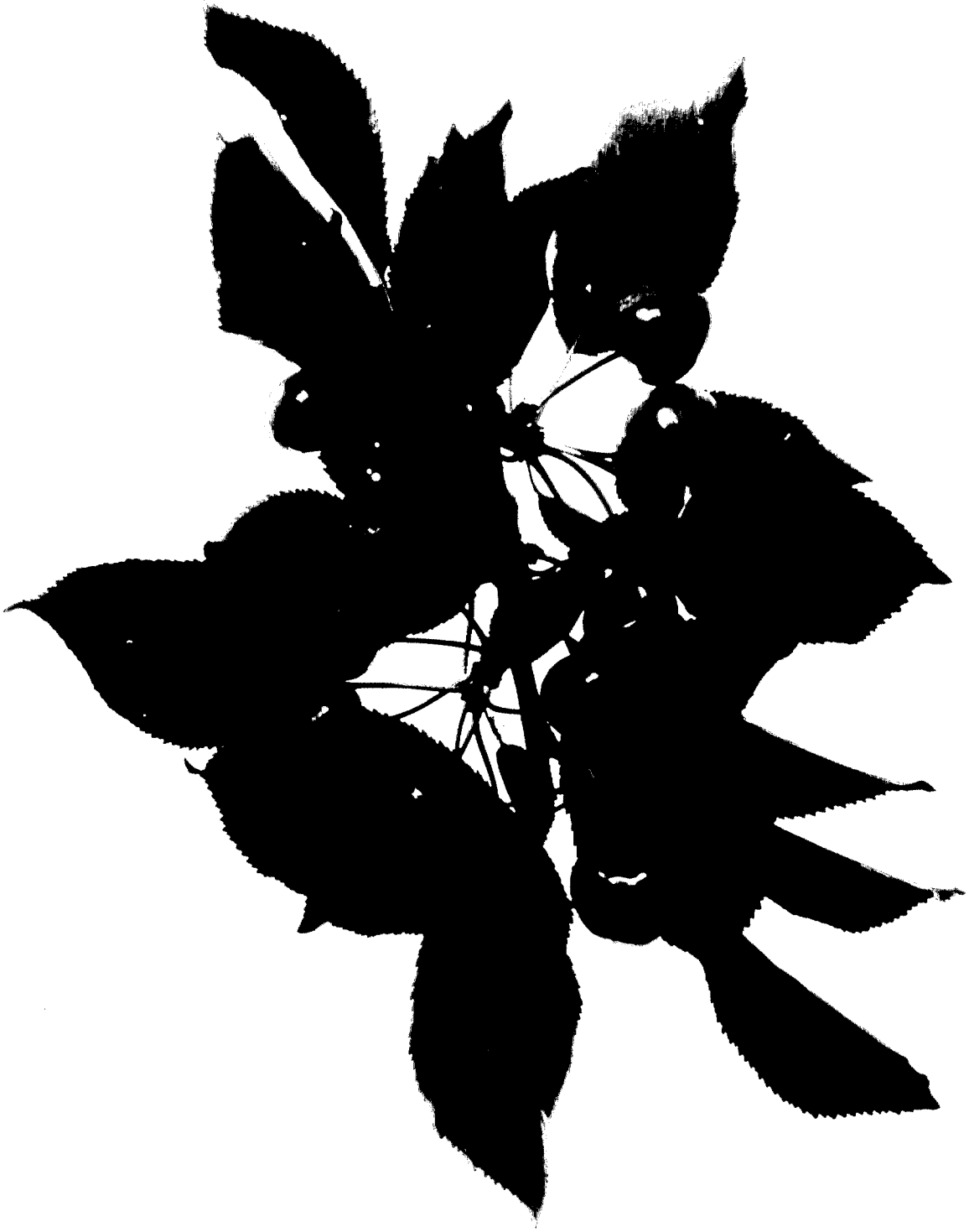

* * * * *